US012779003B2

(12) United States Patent
Saar et al.

(10) Patent No.: US 12,779,003 B2
(45) Date of Patent: Nov. 3, 2026

(54) GRANULATION OF TOPINAMBUR

(71) Applicant: Begapinol Holding GmbH, Berchtesgaden (DE)

(72) Inventors: Ingo Saar, Niederkassel (DE); Marcus Heidenreich, Bad Reichenhall (DE)

(73) Assignee: Begapinol Holding GmbH, Berchtesgaden (DE)

( * ) Notice: Subject to any disclaimer, the term of this patent is extended or adjusted under 35 U.S.C. 154(b) by 923 days.

(21) Appl. No.: 17/768,080

(22) PCT Filed: Oct. 6, 2020

(86) PCT No.: PCT/EP2020/000172
§ 371 (c)(1),
(2) Date: Apr. 11, 2022

(87) PCT Pub. No.: WO2021/069090
PCT Pub. Date: Apr. 15, 2021

(65) Prior Publication Data

US 2024/0000877 A1 Jan. 4, 2024

(30) Foreign Application Priority Data

Oct. 11, 2019 (EP) .................................... 19000465

(51) Int. Cl.
*A61K 36/28* (2006.01)
*A61J 3/00* (2006.01)

(52) U.S. Cl.
CPC ................ *A61K 36/28* (2013.01); *A61J 3/00* (2013.01)

(58) Field of Classification Search
None
See application file for complete search history.

(56) References Cited

U.S. PATENT DOCUMENTS

| | | | | | |
|---|---|---|---|---|---|
| 5,904,937 | A | * | 5/1999 | Augello | A61K 31/192 424/494 |
| 2008/0107788 | A1 | | 5/2008 | Silver | |
| 2019/0167592 | A1 | | 6/2019 | Jain et al. | |

FOREIGN PATENT DOCUMENTS

| | | | | | |
|---|---|---|---|---|---|
| CN | 101245353 | A | | 8/2008 | |
| CN | 103608036 | A | | 2/2014 | |
| CN | 104543833 | A | | 4/2015 | |
| CN | 104938895 | A | | 9/2015 | |
| CN | 106889625 | A | | 6/2017 | |
| CN | 107411065 | A | | 12/2017 | |
| DE | 69520528 | T2 | | 9/2001 | |
| DE | 101 01 871 | A1 | | 7/2002 | |
| DE | 102007032832 | A1 | * | 1/2009 | C12G 3/02 |
| UA | 27401 | U | | 10/2007 | |
| WO | WO 2010/058104 | A2 | | 5/2010 | |

OTHER PUBLICATIONS

Morin G, Briens L. A comparison of granules produced by high-shear and fluidized-bed granulation methods. AAPS PharmSciTech. Aug. 2014;15(4):1039-48. doi: 10.1208/s12249-014-0134-7. Epub May 17, 2014. PMID: 24839117; PMCID: PMC4113627. (Year: 2014).*

Die Topinambur Manufaktur, Jerusalem artichokes granules organic https://www.topinambur-manufaktur.de/Jerusalem-artichokes-granules-organ [retrieved on Oct. 1, 2024] (Year: 2015).*

Morin G., Briens L., A Comparison of Granules Produced by High-Shear and Fluidized-Bed Granulation Methods, AAPS PharmSciTech, vol. 15, No. 4, Aug. 2014 DOI: 10.1208/s12249-014-0134-7 (Year: 2014).*

Gavin K. Reynolds, Phung K. Le, Amol M. Nilpawar, Chapter 1 High shear granulation, Handbook of Powder Technology, Elsevier Science B.V., vol. 11, (2007), https://doi.org/10.1016/S0167-3785(07)80036-4. (Year: 2007).*

Collette technologies, Mixing and Granulation, GEA Pharma Systems, Published May 17, 2017, https://web.archive.org/web/20170517012102/https://photos.labwrench.com/equipmentManuals/15640-6031.pdf (Year: 2017).*

English Translation from Espacenet. Amthor et al., DE-102007032832-A1, Published Jan. 22, 2009, https://translationportal.epo.org/emtp/translate/?ACTION=description-retrieval&COUNTRY=DE&ENGINE=google&FORMAT=docdb&KIND=A1&LOCALE=en_EP&NUMBER=102007032832&SRCLANG=de&TRGLANG=en (Year: 2009).*

Database GNPD [Online] MINTEL; Jan. 18, 2018 (Jan. 18, 2018), anonymous: "Jerusalem Artichoke Granules with Fibre Inulin + Potassium," XP55668045, Database accession No. 5389993, abstract.

Database GNPD [Online] MINTEL; Nov. 21, 2016 (Nov. 21, 2016), anonymous: "Jerusalem Artichoke Dietary Supplement," XP55770068, Database accession No. 4430597, abstract.

Database GNPD [Online] MINTEL; May 15, 2019 (May 15, 2019), anonymous: "Jerusalem Artichoke Kisel with Fructose," XP55770062, Database accession No. 6552445, abstract.

Fars Kaed Alanazi: "Utilization of date syrup as a tablet binder, comparative study," Saudi Pharmaceutical Journal, vol. 18, No. 2, Apr. 1, 2010 (Apr. 1, 2010), pp. 81-89, XP55668286, Amsterdam, NL. ISSN: 1319-0164, DOI: 10.1016/j.jsps.2010.02.003, cited in the application tables 1-10.

International Search Report and Written Opinion mailed Feb. 8, 2021 in the corresponding International Application No. PCT/EP2020/000172.

Brazilian Search Report Issued in BR112022006716-0 dated Jul. 25, 2025.

C. Zhezhong et al., "Cultivation Techniques for Forage Grasses", Gansu People's Publishing House, Dec 1984, p. 183.

Encyclopedia of Chinese Medicine, Dec. 31, 2016, p. 10.

Chinese Search Report issued in 2020800709416 dated Nov. 8, 2023.

Chinese Search Report issued in 2020800709416 dated Dec. 18, 2024.

(Continued)

*Primary Examiner* — Ali Soroush
*Assistant Examiner* — Afua Bamfoaa Boateng
(74) *Attorney, Agent, or Firm* — Secant IP, P.L.L.C.

(57) ABSTRACT

A process for producing a granulate from a fermented topinambur syrup is disclosed. The product of the process is a free flowable granulate with a high content of carbohydrates such as inulin and fructooligosaccharides. Useful applications of this granulate are disclosed likewise.

3 Claims, No Drawings

(56) References Cited

OTHER PUBLICATIONS

Chinese Search Report issued in 2020800709416 dated Apr. 24, 2025.
G. Cao, "Engineering of Traditional Chinese Medicine", Registration No. (Beijing) 075, Jun. 30, 1994, pp. 554-555.
L. Bin, "Formation of Traditional Chinese Medicine (TCM) Preparations", China Medical Science and Technology Publishing House, Jan. 31, 2023, p. 529.
W. Zhijun, "Animal Health Supervision & Quarantine", China Agricultural Science and Technology Press, Dec 31, 1998, p. 531.

* cited by examiner

GRANULATION OF TOPINAMBUR

CROSS-REFERENCE TO RELATED APPLICATIONS

This application is the National Stage entry under 35 U.S.C. § 371 of International Application No. PCT/EP2020/000172, filed on Oct. 6, 2020, published on Apr. 15, 2021 under Publication Number WO 2021/069090 A1, the entirety of which is herein incorporated by reference.

In livestock farming animals are often bred under limited space conditions. This leads to a high vulnerability of the animals towards bacterial infections, with the consequences of serious economic losses for the breeders. To counteract these bacterial infections large amounts of antibiotics are fed to the animals. This way, antibiotics get into the food chain. The biggest problem, however, is the development of antibiotic resistance. Such resistant germs are a massive threat to the efficacy of antibiotics in the treatment of bacterial infections of humans and animals. Therefore, there is a need to find solutions for diminishing or completely avoiding the use of antibiotics in livestock farming.

One approach is the use of prebiotics. Prebiotics are non-digestible fiber substances used as a substrate for beneficial bacteria which promote the growth of the intestinal bacterial microflora.

These beneficial bacteria may hamper the growth of pathogenic bacteria. Thus, there will be less infections and/or inflammations caused by pathogenic germs. In consequence, the amount of antibiotics added to the livestock food can be considerably lowered or even waived.

One of the most popular prebiotics is inulin. Inulin is contained in many plants as a storage polysaccharide and is typically found in roots or rhizomes. Plants with a high content of inulin include a.o. agave, asparagus, banana, burdock, camas, chicory, coneflower, costus, dandelion, elecampane, garlic, globe artichoke, Jerusalem artichoke (topinambur), jicama, leek, leopard's bane, mugwort root, oat, onion, plantain, soybean, wheat, wild yam, and yacón.

For industrial uses, it is most often won from Jerusalem artichoke tubers, also from chicory (*Cichorium intybus*). The Jerusalem artichoke (*Helianthus tuberosus*) is a perennial herbaceous plant of the Asteraceae family originating from North America. It is mostly known as topinambur.

The tubers consist of water (75-79%), carbohydrates (15-16%), proteins (2-3%), fat (2-3%) and microelements up to 0.5% of the fresh weight (Negro et al. (2006) *Appl Biochem Biotechnol* 132: 922-932). Among the carbohydrates, inulin constitutes 80% or more. The remaining sugars are mostly fructose, sucrose and glucose (Kaldy et al. (1980) *Econ Bot* 34: 352-357).

Inulin is a polysaccharide mixture classified as a fructan. It consists of up to 100 fructose monomers and one terminal glucose monomer. It is a linear polymer of D-fructose connected by β (2,1) glycosidic linkages that are terminated by D-glucose molecules bonded to fructose by (2→1) α-bond (De Leenheer (1996) in: van Bekkum et al. (eds) Carbohydrates as organic raw materials Ill, Wiley). The degree of polymerization (DP) depends on cultivation conditions and can range from 2-60 fructose residues. It is a water-soluble fiber first found in the stems of topinambur before it is transferred to the tubers (Negro et al. (2006) *Appl Biochem Biotechnol* 132: 922-932).

Inulin is indigestible by the human small intestine digestive enzymes but is fermented by certain bacteria (e.g. *Bifidobacterium* and *Lactobacillus*) in the large intestine by lactate and short-chain fatty acids (Alles et al. (1996) *Brit J Nutr* 76: 211-221). Thus, it changes the composition of the gut microflora.

Inulin and its hydrolysates were found to selectively stimulate the growth of naturally occurring bifidobacteria in the human colon (Gibson et al. (1995) *Gastroenterology* 108: 975-982; Roberfroid et al. (1998) *J Nutr* 128: 11-19).

Bifidobacteria are thought to promote positive health effects such as reducing cholesterol levels in blood, lowering ammonia levels in blood, inducing the production of vitamins of the B group such as folic acid, rebuilding the gut microflora after a therapy with antibiotics, and inhibiting the growth of pathogenic bacteria by the production of short-chained fatty acids (SCFA) such as acetate, propionate and butyrate (cf. Gibson and Roberfroid (1995) *J Nutr* 125: 1401-1412). Several studies could show that an oral application of inulin augmented the production of butyrate (Scheppach et al. (1992) *J Parenter Enteral Nutr* 16: 43-48; Scheppach et al. (1995) *Eur J Cancer* 31A: 1077-1080; Younes et al. (1996) Br J Nutr 75: 301-314; Campbell et al. (1997) *J Nutr* 127:130-136).

Pathogenic bacteria such as *E. coli* ssp., *Clostridium* ssp., *Salmonella* spp., *Campylobacter, Bacteroides* spp., *Enterococcus, Enterobactericea, Proteus* spp. are hampered in their growth by SCFA (cf. Gibson and Wang (1994) *FEMS Microbiol Lett* 118:121-127).

The beneficial effect of an inulin-containing diet on the gut microflora of ruminants and non-ruminants were described by Samanta et al., (2012) Braz J Microbiol 44: 1-14. Among them are poultry, chicken, geese, ducks, horses, donkeys, rabbits, pigs, cattle, calves, cows, buffaloes, sheep, goats, gayals and camels. By needs this also holds true for bred Indian runner ducks, turkeys, guinea fowls, pigeons, ostrichs, mules, zebus, yaks, dromedaries and lamas. In pigs having inulin a feed additive the burden of intestinal worms was significantly lower (Petkevicius et al. (1997) *Parasitol* 114: 555-568).

A food composition for horses for improving the gut microflora was described in DE 10 2008 006 363 A1. This food composition consists of two components. One of them is a prebiotic component such as topinambur.

Inulin products are marketed as Raftiline St® (mean DP: 10) and Raftiline HP® (mean DP: 20-25).

In a nutrition study in diabetic rats with topinambur tubers a reduction in serum glucose levels, total cholesterol, LDL cholesterol and triglycerides was found (Zacky et al. (2009) *Environ Sci* 5: 682-688). In steptozotocin (STZ)-induced diabetic rats a topinambur treatment led to a relief of diabetic symptoms by repairing the liver damage caused by STZ (Wang et al. (1997) *Arch Toxicol* 71: 638-645).

In herbal and folk medicine the use of topinambur, respectively of inulin is widely known. Beneficial effects were described for example in the treatment of type 1 diabetes and type 2 diabetes (Malten (1954) *Hippokrates* 25: 773-774; Zhuk and Zelenkov (1997) *Vopr Pitan* 6: 34-36), bone fractures (Abrams et al. (2005) *Am J Clin Nutr* 82: 471-476), skin wounds, swelling, pain (cf. Talipova (2001) *Chem Nat Compd* 37: 21-215; Baba et al. (2005) *Tohoku Pharm Univ* 52: 21-25; Yang et al. (2015) *Biotechnol Rep* 5: 77-88), metabolic syndrome (Kumar et al. (2016) *Br J Nutr* 116: 1502-1511), methotrexate-induced liver toxicity (Kalantari et al. (2019) *Biomed Pharmacother* 110: 943-950), colon cancer (Reddy et al. (1997) *Carcinogenesis* 18: 1371-1374), breast cancer, lung cancer, epithelial cancer (cf. Yuan et al. (2013) *Phytochem Lett* 6: 21-25; Kareb et al. (2018) Probiotics and Antimicrobial Proteins: 1-22; Nizioł-Łukaszewska et al. (2018) *Lipids Health Dis* 17: 280).

An absorption of inulin leads to an improved calcium balance, a major goal in osteoporosis prevention (Luo et al. (1996) *Am J Clin Nutr* 63: 939-945).

In combination with bacteriocins such as *Lactobacillus acidophilus* or *Lactobacillus rhamnosus* inulin is able to inhibit the growth of fungi such as *Aspergillus niger* and *Saccharomyces cerevisiae* (Eissa et al. (2018) *AJVS* 59: 17-25). This way inulin can be used in the development of preservative-free food products.

In EP 1269857 A2 a mass is disclosed which is suitable for filling, coating or covering of food products such as cookies, chocolates, sandwiches and potato chips. This mass can contain prebiotic substances such as topinambur.

RU 2377844 C1 reveals a process for producing a topinambur-pear drink as a coffee substitute. A liquid nitrogen extraction is needed and the beverage is achieved by cryocrumbling in precipitated nitrogen.

There is a variety of methods to isolate inulin from topinambur tubers. Optimal conditions for an inulin extraction were 85° C. for 60 minutes with a water solid ratio of 1:20 (v/w). The best yield was achieved by a precipitation with ethanol or acetone. Complete hydrolysis of inulin was achieved at pH 2.0 after 90 minutes at 100° C. (Abozed et al. (2009) *Ann Agric Sci* 54: 417-423).

U.S. Pat. No. 5,968,365 provides a method for clarifying crude inulin extracts with a high degree of polymerization by ultrafiltration. The method encompasses a.o. steps for isolation, enzyme denaturation, clarification, purification and fractionation.

WO 2010/058104 reveals pharmaceutical compositions with an active substance and inulin as the only granulation excipient. These compositions are achieved by wet granulation. A granulation solvent is needed and the ratio between and the active substance is 0.1-0.4.

In WO 2011/128906 A1 a method for producing a taste-masked dry syrup composition of ciprofloxacin is disclosed. To this purpose methacrylate co-polymer in a solvent such as propanol is used.

Alternatively, date syrup can be used as a tablet binder in granulation (Alanazi (2010) *Saudi Pharmac J* 18: 81-89). However, dates are not rich in inulin.

EP 0153447 A1 discloses a process for producing a dry pourable sugar product from a saturated sugar solution by short-time rapid heating in order to produce a syrup which then undergoes rapid crystallization. The process needs to be carried out in a spiral tube with forcible flow-through. Topinambur or Inulin are not mentioned.

WO 2016/210169 discloses a process and system for processing aqueous solutions, among them syrups, in order to generate a supersaturated solution, having over 95% per weight of solids. The process and the equipment are complex and do not refer to topinambur or inulin.

While the beneficial effects of inulin and topinambur are widely acknowledged there is still a lack of a suitable composition for livestock feeding. Topinambur tubers themselves can't be directly fed. Also shredded topinambur tubers are either unappealing to the livestock or the inulin content is too low so that considerable amounts would have to be fed. On the other hand, isolating inulin from topinambur tubers can be a cumbersome procedure. As it must have livestock food quality certain chemical ingredients can't be used for this procedure, or they must be removed afterwards by extra steps. As livestock feeding, respectively meat production are a highly competitive field with narrow profit margins, isolated inulin is not usable for being much too expensive. Therefore there is a need for finding an administration form for inulin that is easy to produce, does not need critical chemicals and above all is suitable for mass production and is inexpensive.

One solution is the provision of a topinambur extract that is undergoing fermentation for conservation. In biology and biotechnology fermentation is defined as a process for the microbial or enzymatic conversion of organic substances into acids, gases or alcohols.

Such a fermentation method for topinambur was disclosed in DE 10 2007 032 832 A1. The inulin content in topinambur tubers of ca. 16% (w/w) can thus be highly increased. The result is a highly concentrated syrup that can be added to the drinking water of the livestock.

This syrup, however, faces serious acceptance problems by the livestock, especially by chickens. The taste, respectively smell of this fermented syrup is apparently strongly repelling for them. The chickens stay widely away from drinking water when this fermented syrup has been added. Therefore insufficient amounts of inulin are ingested. Consequently, the aimed results are not achieved.

Therefore there it was the task to find a composition for a fermented extract from topinambur tubers that overcomes this problem. This task was surprisingly solved by the present invention. It was found that a granulate can be produced from such a fermented extract of topinambur tubers.

The process for producing a granulate from topinambur syrup comprises the following steps:

a) Providing a high shear granulator that comprises a mixed bed, an inlet to the mixed bed, heating means for the mixed bed, a mixer, a homogenizer, a drying bed and heating means for the drying bed,
b) Filling a solid water-insoluble binder suitable for granulation into the mixed bed of a high shear granulator at room temperature and atmospheric pressure,
c) Running the mixer at a mixing velocity of 40 rpm to 120 rpm,
d) Adding a first portion of a topinambur syrup into the mixed bed without running the homogenizer, wherein the ratio of the solid water-insoluble binder to the total topinambur syrup is in the range of 4:1 to 2:3 (w/v), and the first portion of the total topinambur syrup amounts to 20%-30% (v/v) of the total topinambur syrup,
e) Setting the temperature of the mixed bed in the range of 5° C. to 40° C.,
f) Starting the homogenizer at a velocity of 60 rpm,
g) Adding further portions of the topinambur syrup at portions of 1% to 15% (v/v) of the total topinambur syrup until the total topinambur syrup is added,
   wherein a subsequent portion of the topinambur syrup is added after homogeneity of the mixture has been reached,
h) Conveying the granulate to the drying bed, and
i) Drying the granulate at a temperature of 10° C. to 40° C. until the water content of the granulate is less than 4% by weight,
   characterized in that the process does not require a wetting step with a granulation liquid, a carrier gas, the addition of excipients, an enzymatic treatment of the topinambur syrup and in that no heating step of the granulation mixture is performed.

The result is a free-flowing topinambur granulate, characterized by a Topinambur granulate, characterized by a content of minimum 30% carbohydrates by weight, minimum 20% solid water-insoluble binder by weight and a water content of less than 4% by weight, wherein the ratio of the solid water-insoluble binder to the overall carbohydrate content is in the range of 3:1 to 2:3 (w/v).

In preferred embodiment the topinambur granulate according to the invention has a carbohydrate content of minimum 40% per weight, more preferred a carbohydrate content of minimum 50% per weight.

The composition of the carbohydrates depends on the fermented topinambur syrup that is used. The inulin content may vary. The syrup may also contain major portions of degradation products of inulin such as fructooligosaccharides as well as other saccharides. It also depends whether enzymatic treatment has been used for producing the fermented topinambur syrup. The method of the invention, however, works independently of the respective carbohydrate composition of the fermented topinambur syrup that is used.

This topinambur granulate according to the invention was found to have substantially a particle size of 0.5 mm to 2 mm in size, as was assessed in a standard gradation test. The particle size distribution showed to be surprisingly homogeneous.

The solid water-insoluble binder according to the method of the invention can be selected from all known non water-soluble binders that are nutritionally, respectively pharmaceutically acceptable excipients. Preferred are microcrystalline cellulose (E 460 (i); MCC) and diatomaceous earth (D.E.; diatomite; kieselgur). Particularly preferred is microcrystalline cellulose.

Microcrystalline cellulose is a naturally occurring polymer composed of glucose units connected by a 1-4 beta glycosidic bond. The degree of polymerization is typically less than 400. By definition, MCC with particle size of less than 5 μm in diameter should not account for more than 10% by weight.

Diatomaceous earth is a naturally occurring, soft, siliceous sedimentary rock that can be crumbled into fine white powder. The typical chemical composition of oven-dried diatomaceous earth contains 80-90% silica, 2-4% alumina and 0.5-2% iron oxide. The typical particle size ranges from 10 to 200 μm in diameter.

A high-shear granulator (blender, mixer) disperses, or transports, one phase or ingredient (liquid, solid, gas) into a main continuous phase (liquid), with which it would normally be immiscible. A rotor or impeller, together with a stationary component known as a stator, or an array of rotors and stators, is used either in a tank containing the solution to be mixed, or in a pipe through which the solution passes, to create shear. It is used a.o. in the food and pharmaceutical industries for emulsification, homogenization, particle size reduction, and dispersion.

The mixing velocity of the mixed bed for mixing the solid water-insoluble binder and the first portion of the topinambur syrup is in the range of 40 rpm (rounds per minute) to 120 rpm, preferred 50 rpm to 80 rpm, most preferred 55 rpm to 70 rpm.

The mixer can be any mixing device known in the art. Usually, it is an impeller.

The first portion of the topinambur syrup amounts to 20% to 30% (v/v) of the total topinambur syrup, preferred 25% to 30% (v/v), most preferred 30% (v/v).

The ratio of the solid water-insoluble binder to the total topinambur syrup is in the range of 3:1 to 2:3 (w/v), preferred 2:1 to 1:1.25 (w/v), more preferred 1.5:1 to 1:1.1 (w/v), most preferred 1:1 (w/v).

The temperature of the mixed bed is set to 5° C. to 40° C., preferred 25° C. to 40° C., more preferred 30° C. to 40° C. and most preferred 35° C. to 38° C.

When the homogenizer is started it is run at a velocity of 60 rpm. Optionally, the homogenizer can comprise additional grid and/or chopper parts.

Further portions of the topinambur syrup are added at portions of 1% to 15% (v/v) of the total topinambur syrup until the total topinambur syrup is added, preferred at portions of 2% to 10% (v/v), most preferred at portions of 5% (v/v). A subsequent portion of the topinambur syrup is added after homogeneity of the mixture has been reached. In general, the state of homogeneity is estimated by the operator by eyesight. Alternatively, technical means known in the art can be used instead. Normally, a next portion is thus added after 0.5 min to 5 min, preferred after 1.5 min to 4 min, most preferred after 2.5 min to 3 min.

Optionally, the granulation process can be monitored via an ampere meter. When granulation is reached the current increases to a characteristic value. Thus the granulation process can be monitored.

The resulting granulate is conveyed out of the mixed bed by opening a sliding window. The movement of the mixer conveys the granulate continuously out of the mixed bed. It is received on drying means. In most cases these are drying trays. These drying trays are usually set into a drying chamber.

The drying temperature is in the range of 10° C. to 40° C., preferred 20° C. to 40° C., more preferred 30° C. to 38° C., most preferred 35° C.

Surprisingly, it turned out that the granulate according to the invention could be produced without adding a granulation liquid. In wet granulation processes such as fluid bed granulation, blender granulation and compaction there is always one or more granulation liquids that need to be added. The granulation liquid contains a solvent or carrier material which must be volatile which is going to be removed during the drying step. Common granulation liquids are water, ethanol, isopropanol, acetone and aqueous solutions of them, or polyvinyl pyrrolidone (PVP), In wet granulation processes a heating step is usually included in order to evaporate the granulation liquid. As the method according to the invention works without a granulation liquid such a heating step is moot. Therefore the process according to the invention is further characterized in that no heating step of the granulation mixture is performed.

The process according to the invention is characterized in that no carrier gases such as air, nitrogen, inert gases or hydrogen are needed.

In a variety of topinambur-processing methods enzymes such as inulinase (beta-fructofuranosidase), pectinase, sucrase, alpha-amylase, maltase, fructosyltransferase or invertase are added to break down the polysaccharide structure to oligo- or monosaccharides (e.g. DE 4426662 C2). Such a treatment is not needed during the granulation process according to the invention. Therefore the process according to the invention is further characterized in that no enzymatic treatment of topinambur is needed.

Excipients used in wet granulation typically include diluents, binders, disintegrants and lubricants, while other stabilizing agents and pigments may also be included. Typical excipients for wet granulation include, without being limiting, hydroxypropylmethylcellulose (HPMC), carboxymethylcellulose (CMC), xanthan gum, sugar, gelatin, polyvinyl pyrrolidones, acrylates, maltodextrin, lactose monohydrate, sucrose, and starches. Surprisingly, none of these excipients is needed for granulation of the fermented topinambur syrup. Therefore the process according to the invention is further characterized in that no addition of excipients is needed.

In another aspect the present invention relates to the use of the topinambur granulate according to the invention as a food additive in livestock farming.

Such livestock is selected from a group comprising, without being limiting, poultry, chicken, geese, ducks, turkeys, rabbits, pigs, calves and cows. Preferred is the use for chickens.

In a further aspect the present invention relates to the use of the topinambur granulate according to the invention as a diagnostic agent to measure kidney function by determining the glomerular filtration rate. Inulin as a major component of topinambur is an established tool in diagnostics and monitoring of disease progression in chronic kidney disease. The determination of inulin clearance is regarded as one of the best and most precise methods. Inulin is filtered by the glomeruli. It is neither reabsorbed nor secreted in the renal tubules. There is no metabolic degradation either. Thus it just passes inertly through the kidney and can be easily quantified.

Based on this measurement the glomerular filtration rate (GFR) can be calculated (cf. K/DOQI clinical practice guidelines for chronic kidney disease: evaluation, classification, and stratification. In: *American Journal of Kidney Diseases* (2002) 39: S1-266; Kim et al. (2015) *Clin Nephrol* 84: 331-338). Instead of isolated inulin the topinambur granulate can be given to such a patient.

Topinambur, respectively inulin formulations are widely used as prebiotic dietary supplements (cf. Rubel et al. (2014) *Food Res Int* 62: 59-65; Szewczyk et al. (2019) *Ann Agric Envir Med* 26: 24-28). Examples include dietary supplement powders, injections, pellets, capsules, tablets, drops, granules as well as additives to food products such as yogurts. Therefore the present application refers also to the use of the topinambur granulate according to the invention as a prebiotic dietary supplement.

Therefore the present application refers also to the topinambur granulate according to the invention for use in medicine.

In particular, the present application refers also to the topinambur granulate according to the invention for use in the prophylaxis and treatment of bone fractures, skin wounds, swelling, pain, breast cancer, lung cancer, colon cancer, epithelial cancer, metabolic syndrome, methotrexate-induced liver toxicity, type 1 diabetes, type 2 diabetes, osteoporosis, and mycoses.

In another aspect the present application refers to a pharmaceutical composition comprising the topinambur granulate according to the invention and at least one pharmaceutically acceptable excipient. For example, the topinambur granulate according to the invention could be used in capsules or tablets.

The term "pharmaceutically acceptable excipient" refers to a natural or synthetic compound that is added to a pharmaceutical formulation alongside the topinambur granulate according to the invention. They may help to bulk up the formulation, to enhance the desired pharmacokinetic properties or the stability of the formulation, as well as be beneficial in the manufacturing process.

The at least one suitable pharmaceutically acceptable excipient can be selected from the group comprising, without being limiting, carriers, binding agents, lubricants, glidants, disintegrants, colorants, preservatives, antioxidants, acidifiers, thickening agents, fillers, aromatic and flavoring substances, sweeteners.

Eligible are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethylglycols, fatty acid esters of sorbitan.

The term binding agents refers to substances that bind powders or glue them together, rendering them cohesive through granule formation. They serve as a "glue" of the formulation. Binding agents increase the cohesive strength of the provided diluent or filler.

Suitable binding agents are for example starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminum silicate, waxes and others. The percentage of the binding agent in the composition can range from 1-30% by weight, preferred 2-20% by weight, more preferred 3-10% by weight and most preferred 3-6% by weight.

The term lubricants refers to substances that are added to the dosage form in order to facilitate tablets, granulates etc. to be released from the press mold or the outlet nozzle. They diminish friction or abrasion. Lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more preferred between 0.3 and 3% per weight, most preferred between 0.3 and 1.5% per weight.

Suitable lubricants are a.o. sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol.

Glidants are materials that prevent a baking of the respective agents and improve the flow characteristics of granulations so that the flow is smooth and constant. Suitable glidants comprise silicon dioxide, magnesium stearate, sodium stearate, starch and talcum. The amount of the glidant in the composition may vary between 0.01 and 10% per weight, preferred between 0.1 and 7% per weight, more preferred between 0.2 and 5% per weight, most preferred between 0.5 and 2% per weight.

The term disintegrant refers to substances added to a composition in order to facilitate their breaking apart. Suitable disintegrants can be selected from the group comprising starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya (Indian tragacanth), locust bean gum, tragacanth, clays such as bentonite, xanthan gum, alginates such as alginic acid and sodium alginate, foaming compositions a.o. Moisture expansion is supported by for example starch, cellulose derivatives, alginates, polysaccharides, dextrans, and cross-linked polyvinyl pyrrolidone. The amount of the disintegrant in the composition may vary between 1 and 40% per weight, preferred between 3 and 20% per weight, most preferred between 5 and 10% per weight.

Colorants are excipients that bestow a colorization to the composition of the drink, respectively the dosage form. These excipients can be food colorants. They can be adsorbed on a suitable adsorption means such as clay or aluminum oxide. The amount of the colorant may vary between 0.01 and 10% per weight of the pharmaceutical composition, preferred between 0.05 and 6% per weight, more preferred between 0.1 and 4% per weight, most preferred between 0.1 and 1% per weight.

Suitable pharmaceutical colorants are for example curcumin, riboflavin, riboflavin-5'-phosphate, tartrazine, alkannin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, Indathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminium, silver, gold, pigment rubine, tannin, orcein, ferrous gluconate, ferrous lactate.

Preservatives may be selected from the group comprising, but not limited to, sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl parahydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulphite, sodium bisulphite, sodium metabisulphite, potassium metabisulphite, potassium sulphite, calcium sulphite, calcium hydrogen sulphite, potassium hydrogen sulphite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

Suitable thickening agents can be selected from the group comprising, but not limited to, polyvinyl pyrrolidone, methyl cellulose, hydroxypropyl methyl cellulose, hydroxypropyl cellulose, dextrins, polydextrose, modified starch, alkaline modified starch, bleached starch, oxidized starch, enzyme-treated starch, monostarch phosphate, distarch phosphate esterified with sodium trimetaphosphate or phosphorus oxychloride, phosphate distarch phosphate, acetylated distarch phosphate, starch acetate esterified with acetic anhydride, starch acetate esterified with vinyl acetate, acetylated distarch adipate, acetylated distarch glycerol, distarch glycerin, hydroxypropyl starch, hydroxy propyl distarch glycerin, hydroxypropyl distarch phosphate, hydroxypropyl distarch glycerol, starch sodium octenyl succinate, acetylated oxidized starch, hydroxyethyl cellulose.

Fillers are inactive substances added to drugs in order to handle minimal amounts of active agents. Examples for fillers are water, mannitol, pre-gelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Suitable examples for antioxidants include sodium metabisulfite, alpha-tocopherol, ascorbic acid, maleic acid, sodium ascorbate, ascorbyl palmitate, butylated hydroxyanisol, butylated hydroxytoluene, fumaric acid or propyl gallate. Preferred is the use of sodium metabisulfite.

Acidifiers use to be inorganic chemicals that either produce or become acid. Suitable examples are: Ammonium chloride, calcium chloride.

Suitable aromatic and flavoring substances comprise above all essential oil that can be used for this purpose. In general, this term refers to volatile extracts from plants or parts of plants with the respective characteristic smell. They can be extracted from plants or parts of plants by steam distillation.

Examples are: Essential oils, respectively aromatic substances from sage, cloves, chamomile, anise, star anise, thyme, tea tree, peppermint, mint oil, menthol, cineol, *eucalyptus* oil, mango, figs, lavender oil, chamomile blossoms, pine needles, cypress, oranges, rosewood, plum, currant, cherry, birch leaves, cinnamon, limes, grapefruit, tangerine, juniper, valerian, lemon balm, lemon grass, palmarosa, cranberry, pomegranate, rosemary, ginger, pineapple, guava, *echinacea*, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

Suitable sweeteners can be selected from the group comprising, but not limited to, mannitol, glycerol, acesulfame potassium, aspartame, cyclamate, isomalt, isomaltitol, saccharin and its sodium, potassium and calcium salts, sucralose, alitame, thaumatin, glycyrrhizin, neohesperidine dihydrochalcone, steviol glycosides, neotame, aspartame-acesulfame salt, maltitol, maltitol syrup, lactitol, xylitol, erythritol.

EXAMPLES

All granulation experiments were carried out with a fermented topinambur syrup (TopinVet®, Mühldorfer Nutrition AG, Mühldorf/Inn, Germany) having the following composition:

70% soluble dry substance; 71% total dry mass; 1% total acid; 60% total carbohydrates, having 5% inulin, 42% fructooligosaccharides, 8% saccharides, 4% fructose, 1% glucose; 38 g/kg crude ash; 46 g/kg raw protein; 2.2 g/kg crude fiber; <1 g/kg crude oils; 0.06 mg/100 g vitamin A; 0.95 mg/100 g vitamin B1; 0.3 mg/100 g vitamin B2; 6.2 mg/100 g niacin; 20 mg/100 g vitamin C; moisture content 30%. Minerals in mg/100 g in the organic substance: 2013 potassium, 50 magnesium, 123 calcium, 12 iron, 546 phosphor, 13 sodium, 3 nitrate. Neutral smell.

The granulator was a Lödige MGT 250 high shear granulator (Lödige, Paderborn, Germany).

Example 1

10 kg of microcrystalline cellulose (MCC; Avicel® PH-102; DFE pharma, Goch, Germany) was provided in the mixed bed of the high shear granulator at room temperature and atmospheric pressure. The mixing velocity was set to 60 rpm. Then a first portion (3 l) of the fermented topinambur syrup was added. The temperature of the mixed bed was now set to 35° C. When this temperature was reached the homogenizer was started. When homogeneity of the mixture was reached (assessed by eye control) the next portion (1 l) of the fermented topinambur syrup was added. After ca. 3 minutes homogeneity was reached again. This stepwise addition of the fermented topinambur syrup was repeated until 10 l in total of the fermented topinambur syrup was in the mixture. After final homogenization the resulting granulate was conveyed to the drying bed. The temperature of the drying bed was set to 35° C. The drying step was continued until the water content of the granulate was less than 4% by weight (after ca. 3 hours). The water content was assessed with an infrared residual moisture balance (Mettler-Toledo M A 960; Mettler-Toledo GmbH, Giessen, Germany). The result was a homogenous, free-flowing granulate.

Example 2

The experimental setting of Example 1 was mostly maintained but the following process parameters were modified: The mixing velocity of the impeller was set to 100 rpm. The first portion of the fermented topinambur syrup was 2 l, all subsequent portions 500 ml. The temperature of the mixed bed was 38° C. In this setting homogenization was reached after ca. 2.5 min, respectively. The temperature of the drying bed was set to 30° C. Therefore the time of the drying step was ca. 4 hours. The resulting granulate is macroscopically similar to that of Example 1.

Example 3

The experimental setting of Example 1 was mostly maintained but the following process parameters were modified: The mixing velocity of the impeller was set to 40 rpm. The first portion of the fermented topinambur syrup was 3 l, all subsequent portions 500 ml. The temperature of the mixed bed was 30° C. In this setting homogenization was reached after ca. 4 min, respectively. The temperature of the drying bed was set to 40° C. The time of the drying step was ca. 3 hours. The resulting granulate is macroscopically similar to that of Examples 1 and 2.

Example 4

The resulting granulate from Example 1 was analyzed for its particle size by means of sieve analysis (Retsch GmbH, Haan, Germany). It turned out that virtually all particles (at least >95%) were in the size range of 0.5 mm to 2 mm in diameter. The particle size distribution was surprisingly very homogeneous.

Example 5

Three leghorn hens (ca. 2 years old) were kept outdoors in a fenced coop (ca. 2 m×2 m) on a solid sandy soil for two days. They were given their standard food and additionally 20 g of the topinambur granulate of Example 1 (10 g each day), scattered on the soil. It could be observed that all three hens were picking the topinambur granules without distinction to their standard food granules. At the next morning, respectively, nearly all topinambur granules were eaten by the hens. No adverse reactions could be observed.

The invention claimed is:

1. A process for producing a free-flowing fermented topinambur granulate, comprising the following steps:

a. providing a high shear granulator that comprises a mixed bed, an inlet to the mixed bed, heating means for the mixed bed, a mixer, a homogenizer, a drying bed and heating means for the drying bed, b. filling a solid water-insoluble binder suitable for granulation into the mixed bed of the high shear granulator at room temperature and atmospheric pressure, c. running the mixer at a mixing velocity of 40 rpm to 120 rpm, d. adding a first portion of a fermented topinambur syrup into the mixed bed without running the homogenizer, wherein I. the ratio of the solid water-insoluble binder to the total fermented topinambur syrup is in the range of 3:1 to 2:3 (w/v), II. it has a content of minimum 30% (w/w) carbohydrates, minimum 20% (w/w) solid water-insoluble binder, III. a water content of less than 4% (w/w), and IV. the first portion of the total fermented topinambur syrup amounts to 20%-30% (v/v) of the total fermented topinambur syrup, e. setting the temperature of the mixed bed in the range of 5° C. to 40° C., f. starting the homogenizer at a velocity of 60 rpm, g. adding further portions of the fermented topinambur syrup at portions of 1% to 15% (v/v) of the total fermented topinambur syrup until the total topinambur syrup is added, I'. wherein a subsequent portion of the fermented topinambur syrup is added after homogeneity has been reached, h. conveying the fermented topinambur granulate to the drying bed, and i. drying the fermented topinambur granulate at a temperature of 10° C. to 40° C. until the water content of the granulate is less than 4% by weight, j. characterized in that the process does not require a wetting step with a granulation liquid, a carrier gas, an enzymatic treatment of the topinambur syrup; and wherein no further heating step of greater than 40° C. of the fermented topinambur granulate is performed.

2. The process according to claim 1, wherein the solid water-insoluble binder is microcrystalline cellulose or diatomaceous earth.

3. The process according to claim 1 or 2, wherein the weight ratio of the solid water-insoluble binder to the fermented topinambur syrup is 1:1.

* * * * *